(12) United States Patent
Sugahara

(10) Patent No.: US 8,348,891 B2
(45) Date of Patent: Jan. 8, 2013

(54) SURGICAL METHOD AND MEDICAL DEVICE

(75) Inventor: Michihiro Sugahara, Tokyo (JP)

(73) Assignee: Olympus Corporation, Tokyo (JP)

(*) Notice: Subject to any disclaimer, the term of this patent is extended or adjusted under 35 U.S.C. 154(b) by 0 days.

(21) Appl. No.: 12/883,773

(22) Filed: Sep. 16, 2010

(65) Prior Publication Data

US 2011/0190584 A1   Aug. 4, 2011

Related U.S. Application Data

(60) Provisional application No. 61/244,586, filed on Sep. 22, 2009.

(51) Int. Cl.
*A61M 29/00* (2006.01)
*A61M 31/00* (2006.01)

(52) U.S. Cl. ......... 604/101.04; 604/101.05; 604/101.01; 604/103.05

(58) Field of Classification Search .......... 604/96.01, 604/101.01–101.05, 103.05
See application file for complete search history.

(56) References Cited

U.S. PATENT DOCUMENTS

| | | |
|---|---|---|
| 4,884,567 A | 12/1989 | Elliott et al. |
| 5,035,231 A | 7/1991 | Kubokawa et al. |
| 5,297,536 A | 3/1994 | Wilk |
| 5,309,896 A | 5/1994 | Moll et al. |
| 5,336,252 A | 8/1994 | Cohen |
| 5,549,569 A | 8/1996 | Lynn et al. |
| 5,697,916 A | 12/1997 | Schraga |
| 5,725,525 A | 3/1998 | Kordis |
| 5,759,150 A | 6/1998 | Konou et al. |
| 5,968,017 A | 10/1999 | Lampropoulos et al. |
| 6,071,295 A | 6/2000 | Takahashi |
| 6,203,490 B1 | 3/2001 | Krajicek |
| 6,338,710 B1 | 1/2002 | Takahashi et al. |
| 7,398,781 B1 | 7/2008 | Chin |
| 7,485,624 B2 | 2/2009 | Donovan |

(Continued)

FOREIGN PATENT DOCUMENTS

JP   62-035318   2/1987

(Continued)

OTHER PUBLICATIONS

International Search Report from corresponding PCT/JP2010/066321. Oct. 26, 2010. 2 Pages.*

(Continued)

*Primary Examiner* — Victoria P Shumate
(74) *Attorney, Agent, or Firm* — Scully, Scott, Murphy & Presser, P.C.

(57) ABSTRACT

To perform treatment by readily introducing a device causing minimal invasion even where approach from the body surface is difficult, a medical device includes a guide that is inserted into a lumen; a first balloon at a distal end of the guide, connected to a first flow path extending to a proximal end of the guide; a second balloon on the guide, separated from the first balloon on the proximal-end side and connected to a second flow path extending to the proximal end of the guide; a third balloon extending along the guide from a point between the first balloon and the second balloon to the proximal end and having a port for supplying or discharging fluid at the proximal end; and a cleansing flow path having a discharge port between the first balloon and the second balloon and extending to the proximal end of the guide.

5 Claims, 7 Drawing Sheets

U.S. PATENT DOCUMENTS

| | | | |
|---|---|---|---|
| 7,621,867 B2 | 11/2009 | Kara et al. | |
| 7,914,444 B2 | 3/2011 | Moriyama et al. | |
| 2004/0064138 A1 | 4/2004 | Grabek | |
| 2007/0023334 A1 | 2/2007 | Hallstadius et al. | |
| 2007/0255100 A1 | 11/2007 | Barlow et al. | |
| 2008/0167621 A1 | 7/2008 | Wagner et al. | |
| 2008/0275371 A1 | 11/2008 | Hoffman | |
| 2010/0191164 A1 | 7/2010 | Sasaki et al. | |

FOREIGN PATENT DOCUMENTS

| | | | |
|---|---|---|---|
| JP | 64-20836 | | 1/1989 |
| JP | 2-55960 | | 4/1990 |
| JP | 07-265321 | | 10/1995 |
| JP | 08-117232 | | 5/1996 |
| JP | 08-280815 | * | 10/1996 |
| JP | 09-187415 | | 7/1997 |
| JP | 11-276422 | | 10/1999 |
| JP | 2000-176011 | | 6/2000 |
| JP | 2001-519212 | | 10/2001 |
| JP | 2001-340462 | * | 12/2001 |
| JP | 2002-017854 | | 1/2002 |
| JP | 2002-522116 | | 7/2002 |
| JP | 2003-144378 | | 5/2003 |
| JP | 2004-033525 | | 2/2004 |
| JP | 2004-081852 | | 3/2004 |
| JP | 2004-097391 | | 4/2004 |
| JP | 2004-105226 | | 4/2004 |
| JP | 2006-271831 | * | 10/2006 |
| JP | 2007-054333 | | 3/2007 |
| JP | 2007-505680 | | 3/2007 |
| JP | 3143693 | | 7/2008 |
| JP | 2008-540117 | | 11/2008 |
| WO | WO 93/09722 | | 5/1993 |
| WO | WO 96/40368 | | 12/1996 |
| WO | WO 97/10753 | | 3/1997 |
| WO | WO 98/24378 | | 6/1998 |
| WO | WO 99/13936 | | 3/1999 |
| WO | WO 99/60924 | | 12/1999 |
| WO | WO 00/07530 | | 2/2000 |
| WO | WO 01/78809 A1 | | 10/2001 |
| WO | WO 2004/012586 A2 | | 2/2004 |
| WO | WO 2006/058434 A1 | | 6/2006 |
| WO | WO 2008/134457 A1 | | 11/2008 |
| WO | WO 2009/004777 A1 | | 1/2009 |

OTHER PUBLICATIONS

International Search Report dated Oct. 26, 2010.

International Search Report dated Dec. 7, 2010 together with an English language abstract.

International Search Report dated Oct. 19, 2010.

Sosa et al., "A New Technique to Perform Epicardial Mapping in the Electrophysiology Laboratory", Journal of Cardiovascular Electrophysiology, Apr. 29, 2007, vol. 7, Issue 6, pp. 531-536.

U.S. Office Action dated Aug. 16, 2012 issued in related U.S. Appl. No. 12/884,845.

U.S. Office Action dated Aug. 27, 2012 issued in related U.S. Appl. No. 12/757,210.

U.S. Office Action dated Aug. 31, 2012 issued in related U.S. Appl. No. 12/871,172.

* cited by examiner

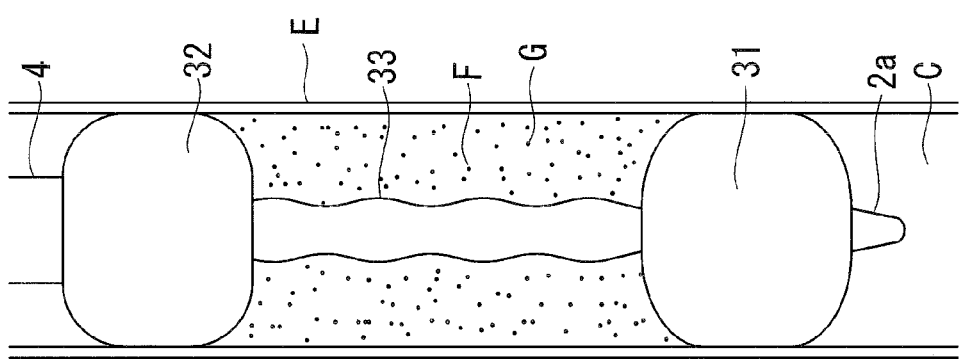
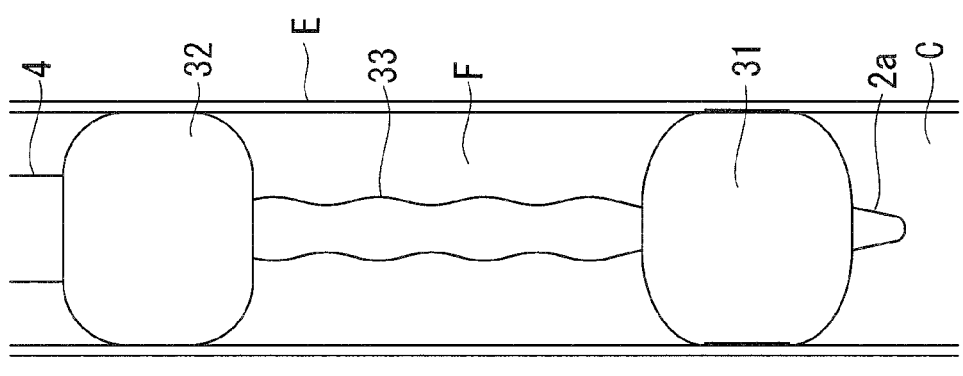
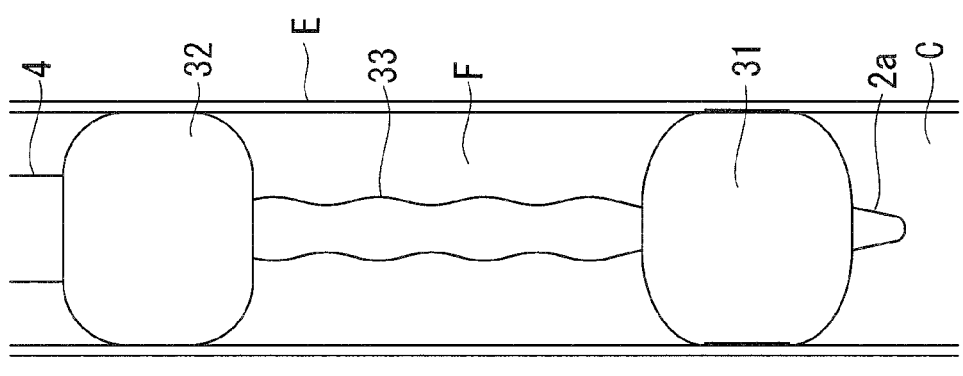
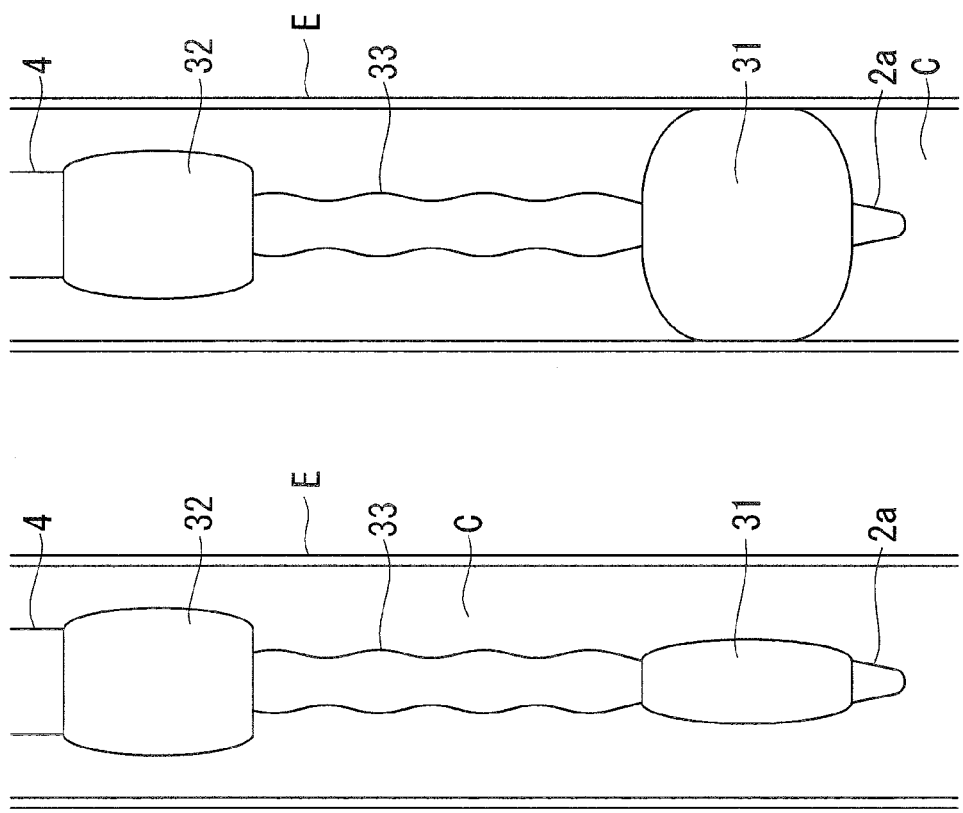

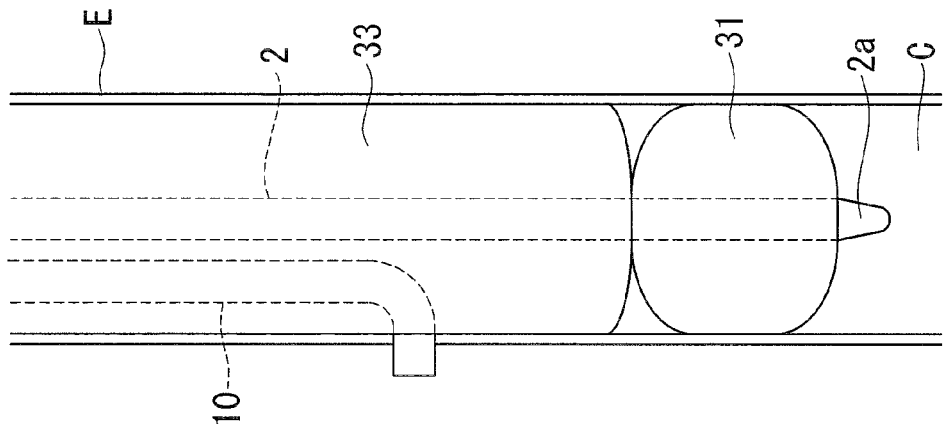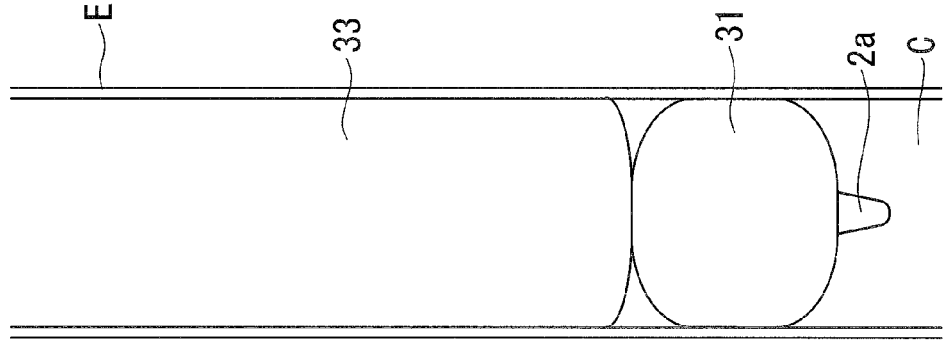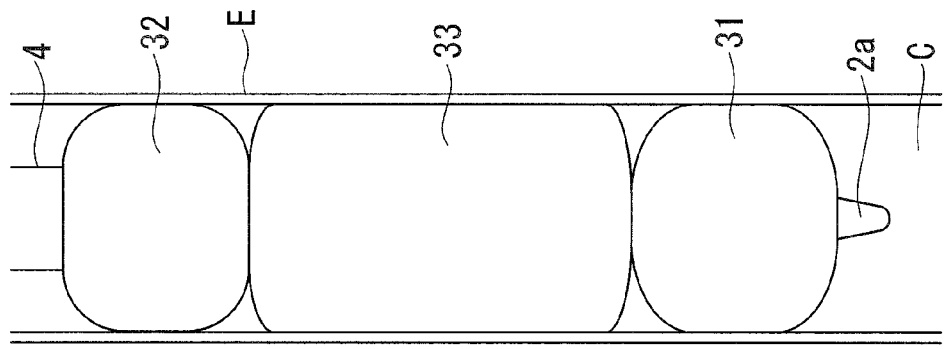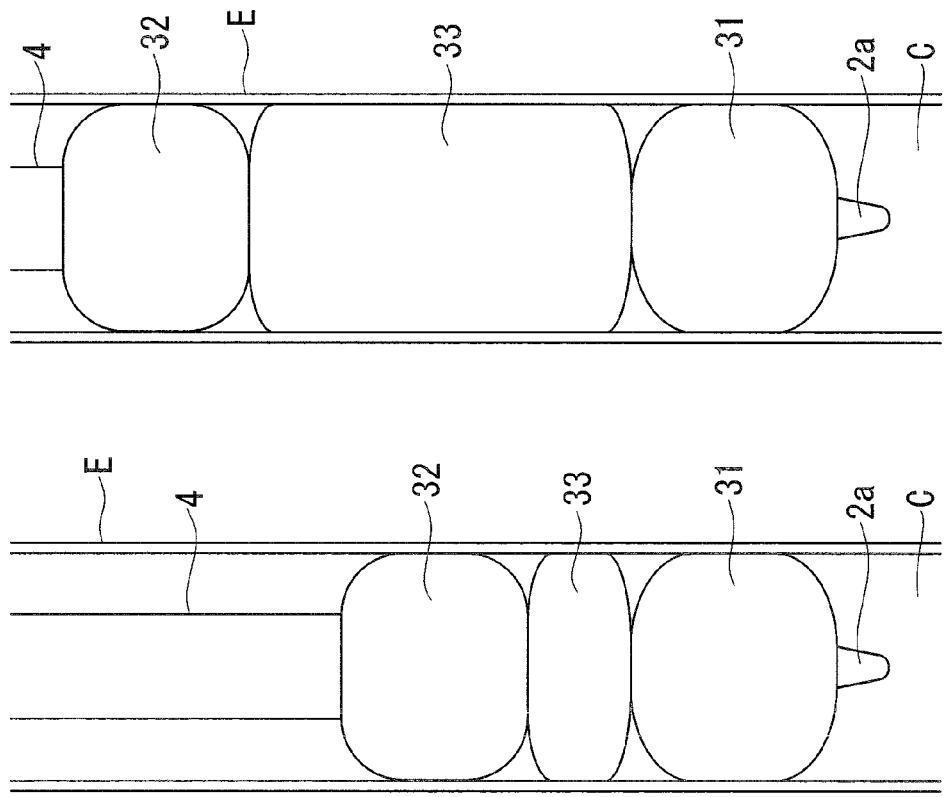

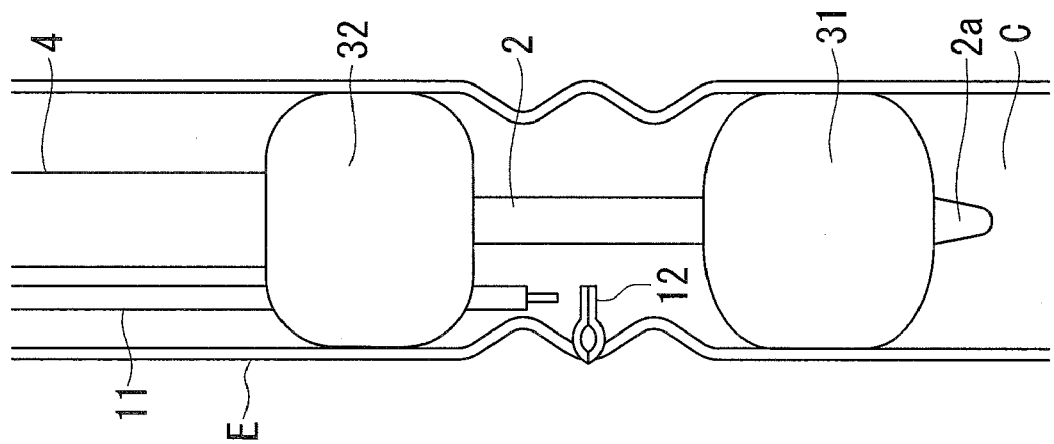
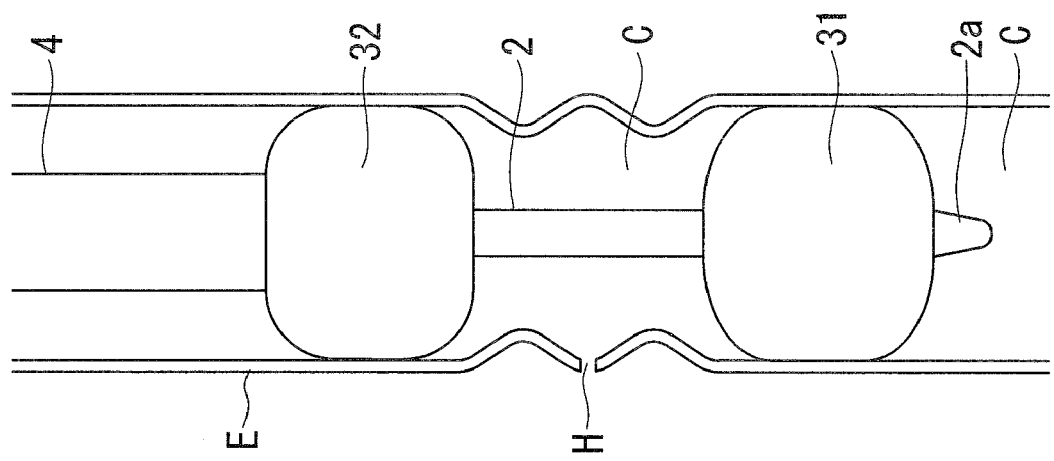
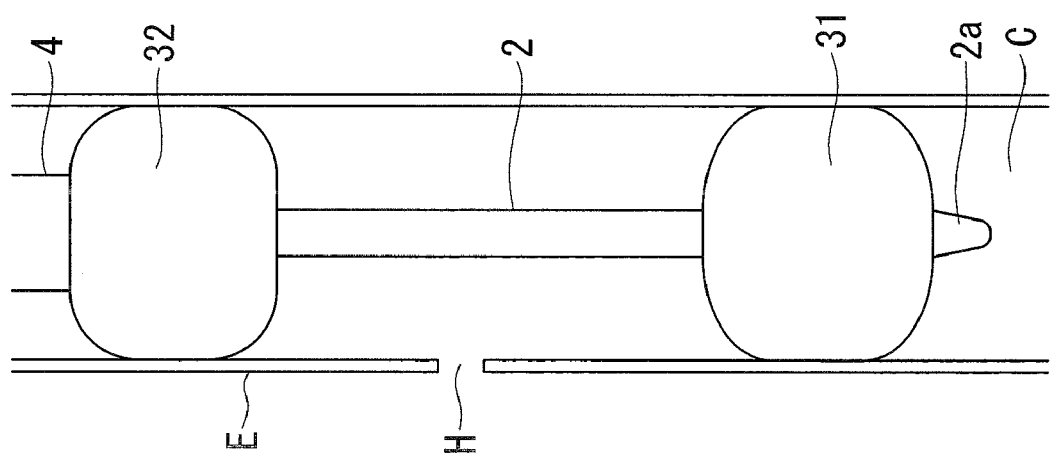

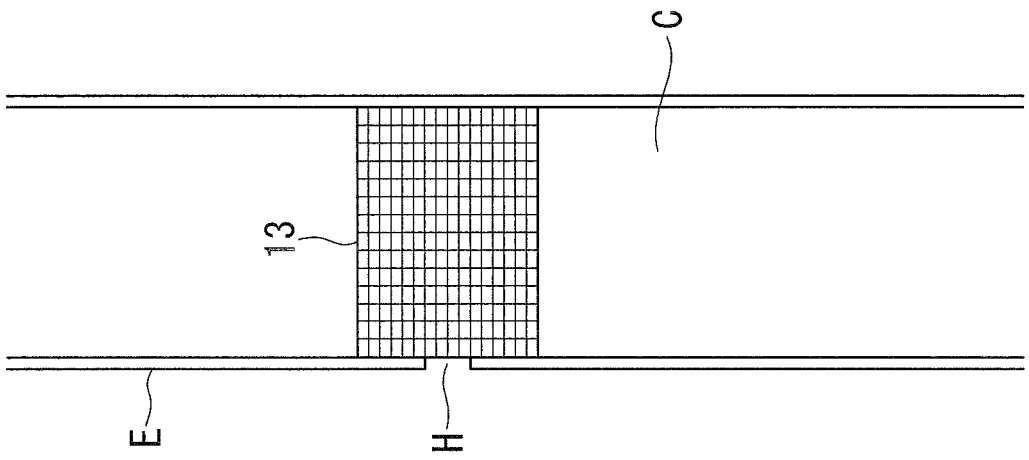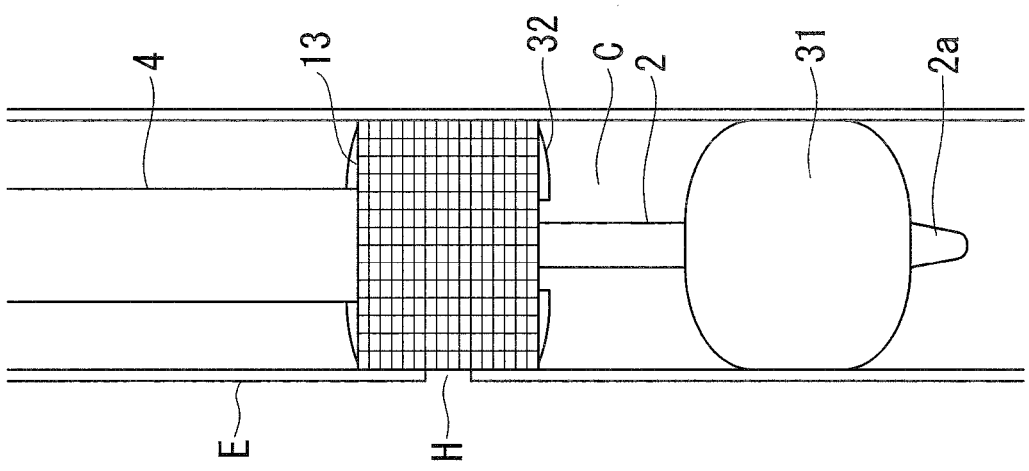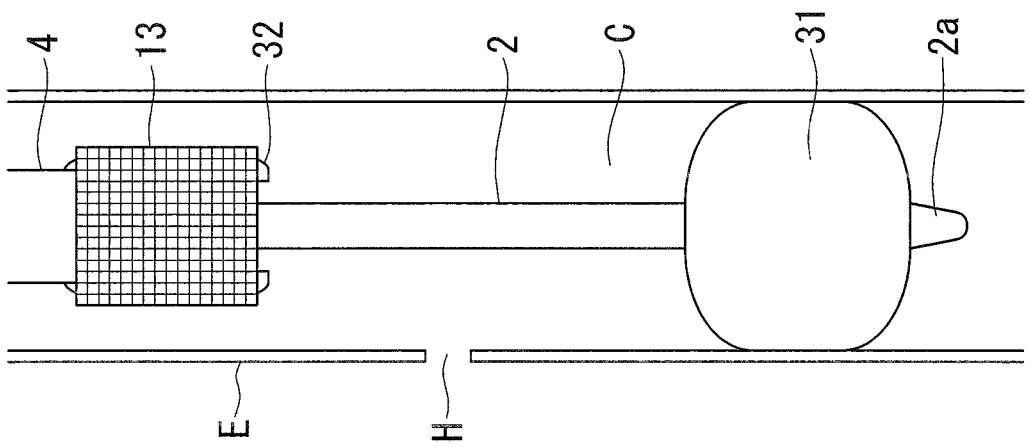

SURGICAL METHOD AND MEDICAL DEVICE

CROSS REFERENCE TO RELATED APPLICATIONS

This application claims the benefit of U.S. Provisional Application No. 61/244,586, filed Sep. 22, 2009, which is hereby incorporated by reference herein in its entirety.

BACKGROUND OF THE INVENTION

1. Field of the Invention

The present invention relates to surgical methods and medical devices.

2. Description of Related Art

When treating the heart with an endoscope or the like, procedures in which a medical device such as an endoscope is introduced into the pericardial cavity from under the xiphoid process are conventionally known (e.g., see U.S. Pat. No. 7,398,781).

In the case of a procedure described in U.S. Pat. No. 7,398,781, the route of the device from under the xiphoid process to an affected area becomes relatively long.

Furthermore, in the supine position, which is a common position for a medical operation, the pericardial cavity on the back side of the heart becomes compressed. In particular, in the vicinity of the pulmonary veins of the left atrium, a sufficient gap that allows insertion of a device between the heart and the pericardium does not exist from the beginning. A site where it is not possible to insert a device via the pericardial cavity, as described above, is usually treated from inside the heart.

BRIEF SUMMARY OF THE INVENTION

It is an object of the present invention to provide a surgical method and a medical device with which it is possible to introduce a device readily and with minimal invasiveness to perform a procedure, even at a site that is difficult to approach from the body surface.

In order to achieve the above object, the present invention employs the following solutions.

A first aspect of the present invention is a surgical method including a cleansing step of cleansing the interior of a lumen passing through the vicinity of an affected area; an inserting step of inserting a surgical device from an opening of the lumen into the interior of the lumen cleansed in the cleansing step; and a penetrating step of penetrating the luminal wall of the lumen with the surgical device in the vicinity of the affected area to advance the surgical device to the affected area.

A second aspect of the present invention is a medical device including a guide member that is inserted into a lumen; a first balloon provided at a distal end of the guide member and connected to a first flow path extending to a proximal end of the guide member; a second balloon provided on the guide member at a point separated from the first balloon on the proximal-end side and connected to a second flow path extending to the proximal end of the guide member; a third balloon extending along the guide member from a point between the first balloon and the second balloon to the proximal end and having a port for supplying or discharging fluid at the proximal end; and a cleansing flow path having a discharge port between the first balloon and the second balloon and extending to the proximal end of the guide member.

BRIEF DESCRIPTION OF THE SEVERAL VIEWS OF THE DRAWINGS

FIGS. 4A to 4H are illustrations for explaining a surgical method according to this embodiment, in which FIG. 4A illustrates a state where the medical device is inserted in the esophagus, FIG. 4B illustrates a state where a first balloon is inflated, FIG. 4C illustrates a state where a second balloon is inflated (closing step), FIG. 4D illustrates a state where a space closed by two balloons is cleansed (cleansing step), FIG. 4E illustrates a state where a third balloon is inflated, FIG. 4F illustrates a state where the third balloon in FIG. 4E is inflated further, FIG. 4G illustrates a state where the third balloon in FIG. 4F is inflated further (route ensuring step), and FIG. 4H illustrates a state where a surgical device inserted through the interior of the third balloon is placed outside the esophageal wall (penetrating step).

FIGS. 5A to 5C are illustrations for explaining a method of closing a puncture hole formed in the esophageal wall after an affected area is treated with the medical device in FIG. 1, in which FIG. 5A illustrates a state where the first and second balloons are inflated at positions on either side of the puncture hole, FIG. 5B is a state where the second balloon in FIG. 5A is moved closer to the first balloon, and FIG. 5C illustrates a state where the puncture hole narrowed in FIG. 5B is clipped.

FIGS. 6A to 6C are illustrations for explaining a method of treating a puncture hole on the esophageal wall with a cover member by using the medical device in FIG. 1, in which FIG. 6A illustrates insertion of the cover member into the esophagus, FIG. 6E illustrates a state where the cover member inserted into the esophagus in FIG. 6A is expanded, and FIG. 6C is a state where treatment with the expanded cover member in FIG. 6B is finished.

DETAILED DESCRIPTION OF THE INVENTION

A medical device 1 and a surgical method performed using the medical device 1 according to an embodiment of the present invention will be described below with reference to the drawings.

Figure 1:
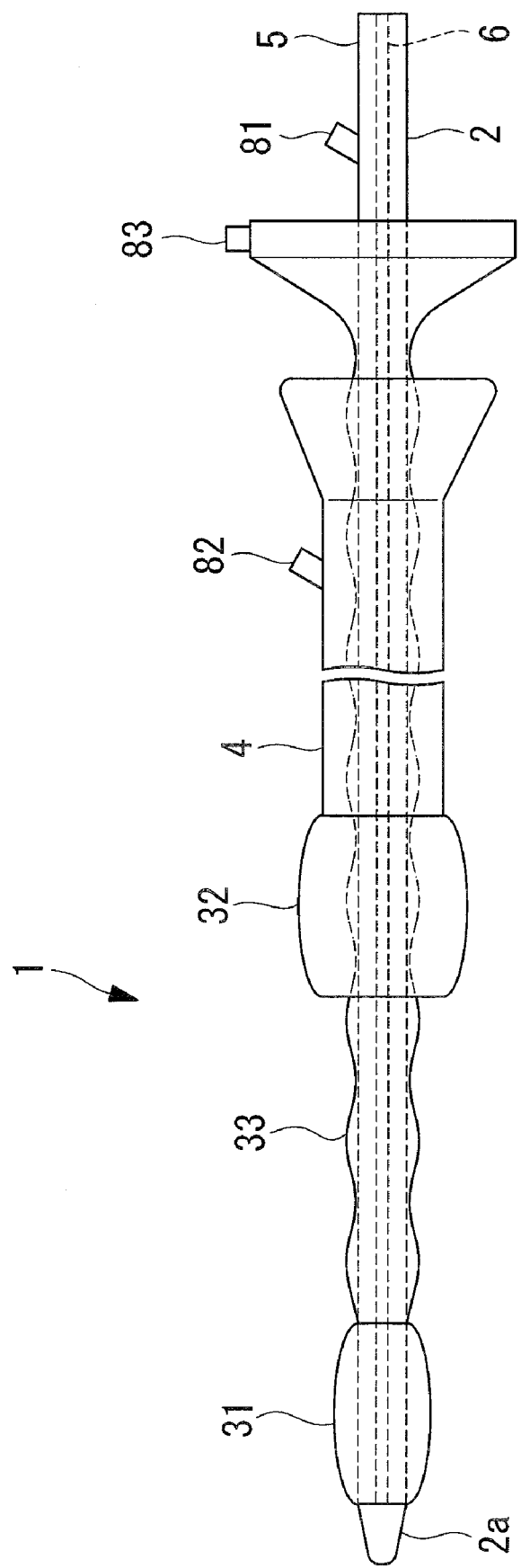
FIG. 1 is an overall configuration diagram of a medical device according to an embodiment of the present invention.

As shown in FIG. 1, the medical device 1 according to this embodiment includes an elongated guide member 2 that can be inserted into a lumen, first and third balloons 31 and 33 provided on the side face of the guide member 2, a sheath 4 in which the guide member 2 is inserted so as to be capable of moving in the lengthwise direction, and a second balloon 32 provided at the distal end of the sheath 4.

The guide member 2 includes a tube 5 and a wire 6 inserted into the tube 5. At the distal end of the guide member 2, a protecting member 2a is provided for protecting a luminal wall when the luminal wall is contacted.

Figure 2:
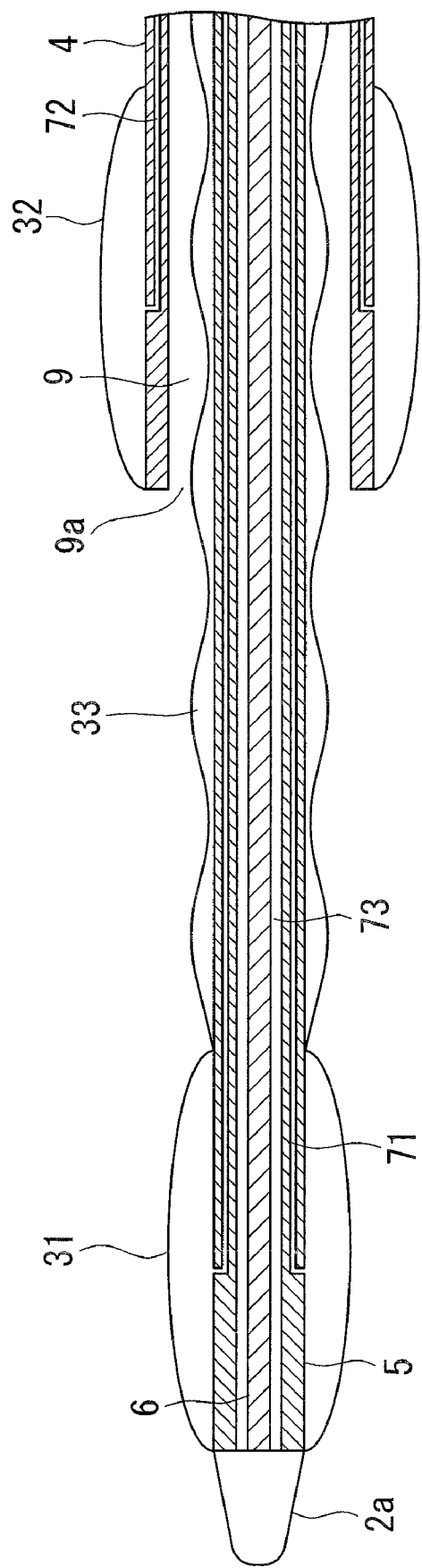
FIG. 2 is a longitudinal section illustrating in detail the configuration of a distal-end portion of the medical device in FIG. 1.

FIG. 2 is a longitudinal section illustrating in detail the configuration of a distal-end portion of the medical device 1.

The first balloon 31 is provided at the distal end of the guide member 2. The third balloon 33 has an elongated shape extending from a point adjacent to the proximal end of the first balloon 31 to the proximal end of the guide member 2. The first and third balloons 31 and 33 cover the entire periphery of the guide member 2 and are inflated substantially with the guide member 2 as a center axis. Here, the first and third balloons 31 and 33 can be inflated to have an outer diameter sufficiently greater than the inner diameter of the lumen in question. The third balloon 33 is configured to be detachable from the guide member 2 by, for example, pulling it toward the proximal end with a relatively large force.

Inside the side wall of the tube 5, a first flow path 71 communicating with the interior of the first balloon 31 is formed along the lengthwise direction. A cylindrical space is formed between the inner circumferential surface of the tube 5 and the outer circumferential surface of the wire 6, constituting a third flow path 73. The third flow path 73 communicates with the interior of the third balloon 33. The first and third flow paths 71 and 73 have first and third ports 81 and 83, respectively, provided on the proximal end of the tube 5. An operator can inflate the balloons 31 and 33 by supplying fluid to the balloons 31 and 33 from the first and third ports 81 and 83 via the flow paths 71 and 73 by using a syringe or the like and applying pressure. Furthermore, after the balloons 31 and 33 are inflated, the operator can restore the balloons 31 and 33 to their deflated states by performing suction through the flow paths 71 and 73.

The sheath 4 has such an inner diameter that a gap is formed between the sheath 4 and the third balloon 33 when it is deflated. The gap constitutes a cleansing flow path 9. The user can discharge cleansing liquid from a discharge port 9a opened at the distal-end face of the sheath 4 by supplying cleansing liquid to the cleansing flow path 9 from another port (not shown) provided at the proximal end of the sheath 4.

The second balloon 32 covers the outer circumferential surface of the sheath 4 in the circumferential direction and is inflated substantially with the sheath 4 as a center axis. Inside the side wall of the sheath 4, a second flow path 72 communicating with the interior of the second balloon 32 is formed along the lengthwise direction. The second flow path 72 has a second port 82 at the proximal end of the sheath 4. Similarly to the first and third balloons 31 and 33, the operator can inflate or deflate the second balloon 32 by supplying or sucking fluid via the second port 82.

Figure 3:
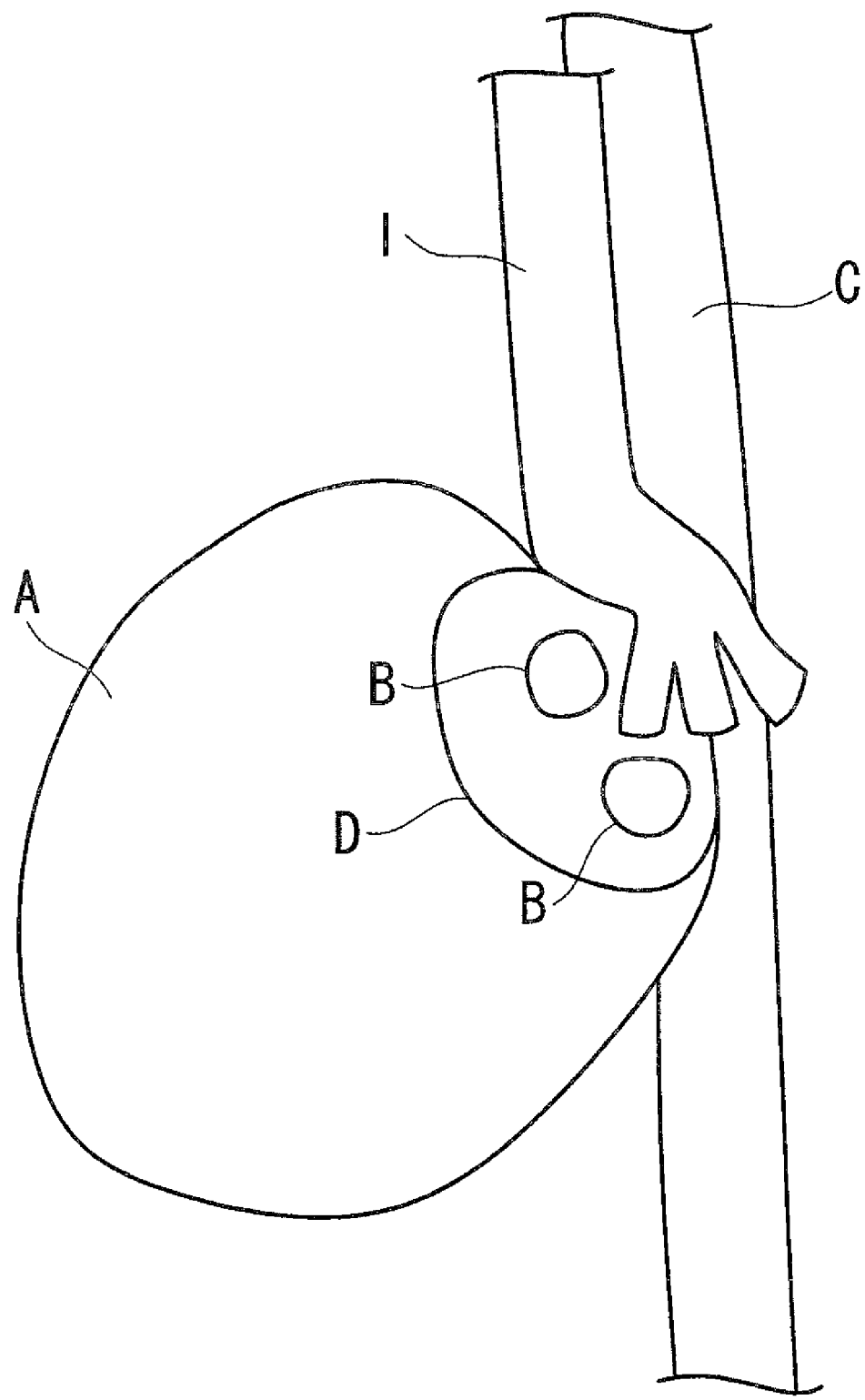
FIG. 3 is an illustration of the positional relationship of the left atrium, the pulmonary veins, and the esophagus.

Next, a surgical method according to this embodiment, performed using the medical device 1, will be described. This embodiment will be described in the context of an example of performing ablation in which the affected area is the joint of the left atrium D and the pulmonary veins B connected to the left atrium D, for example, for treatment of arrhythmia. FIG. 3 illustrates the positional relationship of the heart A, the pulmonary veins B, and the esophagus C. The affected area, i.e., the joint between the pulmonary veins B and the left atrium D, is on the back side of the heart A. Reference sign I denotes the bronchi.

First, with all of the balloons 31, 32, and 33 deflated, the operator inserts the medical device 1 into the esophagus C from the mouth of the patient and places the distal end of the medical device 1 in the vicinity of the affected area with the esophageal wall E in between (see FIG. 4A). Then, the operator inflates the first balloon 31 (see FIG. 4B). At this time, the first balloon 31 is inflated to a sufficient size so that the esophagus C is closed by the first balloon 31 at an intermediate point. Then, the operator inflates the second balloon 32 (see FIG. 4C). Thus, the esophagus C is closed at two points, whereby a closed space F is formed between the two points (closing step).

Then, the operator supplies cleansing liquid to the cleansing flow path 9 to discharge cleansing liquid G from the discharge port 9a into the closed space F, filling the closed space F with the cleansing liquid G (see FIG. 4D). Then, by discharging the cleansing liquid G from the closed space F to the outside of the body through the cleansing flow path 9, it is possible to cleanse the interior of the closed space F (cleansing step). The cleansing liquid G may be supplied and sucked repeatedly a plurality of times as needed.

Then, the operator pushes in the sheath 4 slightly, thereby moving the second balloon 32 closer to the first balloon 31, and then inflates the third balloon 33. Thus, the part of the third balloon 33 existing between the first balloon 31 and the second balloon 32 is inflated (see FIG. 4E). Then, while maintaining the application of pressure to the interior of the third balloon 33, the sheath 4 is withdrawn slowly to the outside of the body (see FIG. 4F). By inflating the elongated third balloon 33 gradually from the distal end to the proximal end as described above, it is possible to inflate the third balloon 33 to a substantially uniform width inside the esophagus C (see FIG. 4G). Accordingly, it is possible to ensure a route separated from the esophageal wall E and the oral cavity wall inside the third balloon 33 from the vicinity of the affected area to the outside of the body (route ensuring step).

Then, the surgical device 10, such as an endoscope, is inserted to the vicinity of the affected area through the interior of the third balloon 33 (inserting step). Then, the surgical device 10 is advanced to the affected area outside the esophagus C by penetrating the third balloon 33 and the esophageal wall E with the surgical device 10 (penetrating step, see FIG. 4H). Then, it is possible to treat the affected area with the surgical device 10.

After treating the affected area, the surgical device 10 is removed to the outside of the body, and the third balloon 33 is removed from the esophagus C while keeping the guide member 2 and the first balloon 31 inside. Then, with the second balloon 32 deflated, the sheath 4 is inserted along the guide member 2. Then, the second balloon 32 is inflated sufficiently at such a position that a puncture hole H formed on the esophageal wall E with the surgical device 10 is located between the first balloon 31 and the second balloon 32 (see FIG. 5A). Then, the second balloon 32 is moved toward the first balloon 31, whereby the esophageal wall E located between the first balloon 31 and the second balloon 32 is contracted in the lengthwise direction (see FIG. 5B). Thus, the puncture hole H is narrowed and almost closed. In this state, a hemostatic clipping device 11 is inserted into the esophagus C to close the puncture hole H with a clip 12. Then, the first and second balloons 31 and 32 are deflated, and the guide member 2 and the sheath 4 are removed from the esophagus C.

As described above, according to this embodiment, the affected area located on the back side of the heart A is approached by the medical device 1 via the esophagus C running inside the body. As opposed to this embodiment, conventionally, when the left atrium D is treated, it has been the case that a device is introduced from the body surface into the body and to insert the device to the left atrium D via the thoracic cavity or the thoracic diaphragm. With this method, it is difficult to move the device since other tissue or the like interferes with the insertion route at intermediate points. Furthermore, the insertion route becomes relatively long, causing considerable invasiveness to the body of the patient. In contrast, according to this embodiment, a short route suffices from the esophagus C to the affected area, so that invasiveness to the body of the patient can be reduced considerably.

Furthermore, in the vicinity of the joint between the left atrium D and the pulmonary veins B, the gap between the wall of the heart A and the pericardium is very small, so that a sufficient gap for inserting an endoscope does not exist. Furthermore, since even the very small space is pressed in the ordinary supine position for a medical operation, it is very difficult to insert a device. In contrast, according to this embodiment, by approaching the affected area with the medical device 1 from outside the heart A, regardless of the operation position of the patient or the size of the pericardial cavity, it is possible to readily advance the medical device 1 to the affected area. Furthermore, for example, it becomes possible to treat the affected area while viewing the surgical device 10 or the affected area with an endoscope, which facilitates the operation.

Furthermore, the esophagus C gets contaminated easily compared with other lumens, so that care must be taken against infection or the like. Therefore, the interior of the esophagus C is segmented with the two balloons 31 and 32 during cleansing, and then a device insertion route separated from the esophageal wall E is ensured with the third balloon 33. Thus, it is possible to prevent the device from being contaminated during insertion or a cleansed region from being recontaminated via the device, keeping the treated area clean. Furthermore, since it suffices to cleanse only a narrow region in the vicinity of a punctured site, the labor associated with cleansing or the burden on the patient associated with cleansing can be reduced.

Although the puncture hole H on the esophageal wall E is closed by clipping in this embodiment, alternatively, the puncture hole H may be closed with a cover member 13, such as a tape. FIGS. 6A to 6C illustrate another method of treating the puncture hole H with the medical device 1 according to this embodiment. The cover member 13 is formed in a ring shape and is expandable in a radial direction at least to the inner diameter of the esophagus C.

After treating the affected area, the third balloon 33 and the surgical device 10 are removed from the esophagus C, and then the cover member 13 is placed on the outside of the deflated second balloon 32 and inserted into the esophagus C to the position of the puncture hole H (see FIG. 6A). Then, the second balloon 32 is inflated to expand the cover member 13 in the radial direction (see FIG. 6B). Thus, the inner surface of the esophagus C is covered with the cover member 13, closing the puncture hole H. Then, the first and second balloons 31 and 32 are deflated, and the guide member 2 and the sheath 4 are removed from the esophagus C, so that only the cover member 13 remains in the esophagus C (see FIG. 6C).

Also in this case, it is possible to treat the puncture hole H in the esophagus C by a simple method with an approach from the oral cavity. In order that the cover member 13 remains at a desired position at least for a certain period until the puncture hole H is closed sufficiently, an adhesive may be applied to the outer surface of the cover member 13. Preferably, the cover member 13 is formed of a biodegradable material so that the cover member 13 naturally falls off the esophageal wall E as time elapses. In this case, it is possible to eliminate the need for a procedure for removing the cover member 13 from the esophagus C.

Although this embodiment has been described in the context of an example where the left atrium D is approached by the medical device 1 from inside the esophagus C, the lumen can be selected as appropriate depending on the position of the affected area. For example, in a case where a procedure is performed on other sites inside the thoracic cavity, the affected area may be approached by the medical device 1 from inside the bronchi I. Also in this case, a site that is difficult to approach either from the back side or the abdominal side of the patient can be approached by the medical device 1 readily and with minimal invasiveness. In a case where a procedure is performed inside the abdominal cavity, the site may be approached by the medical device 1 by penetrating the luminal wall from inside the intestines or the stomach.

The present invention has the following aspects.

A first aspect of the present invention is a surgical method including a cleansing step of cleansing the interior of a lumen passing through the vicinity of an affected area; an inserting step of inserting a surgical device from an opening of the lumen into the interior of the lumen cleansed in the cleansing step; and a penetrating step of penetrating the luminal wall of the lumen with the surgical device in the vicinity of the affected area to advance the surgical device to the affected area.

According to the first aspect of the present invention, the surgical device is inserted into the lumen in the inserting step, and the luminal wall is penetrated with the surgical device in the penetrating step. Thus, it is possible to advance the surgical device from inside the lumen to the affected area located outside the lumen and treat the affected area.

In this case, even at a site for which it has been conventionally difficult to ensure a route for inserting a surgical device from the body surface due to interference by other tissues or the like, it is possible to readily introduce the surgical device from inside a lumen running inside the body of the patient with a relatively short route, which serves to reduce invasiveness to the patient. Furthermore, since it is possible to approach the affected area with the device from the outside, it is possible to readily check the status of the affected area or the procedure. Furthermore, even though the device is introduced to the affected area via the lumen as described above, by cleansing the interior of the lumen in advance, it is possible to treat the affected area under a clean environment.

In the first aspect above, a closing step of closing, prior to the cleansing step, the interior of the lumen at two points spaced apart from each other in the vicinity of the affected area may be further provided, and a closed space formed between the two points in the closing step may be cleansed in the cleansing step.

In this case, it is possible to cleanse only the necessary region efficiently.

In the above configuration, the closing step may be performed by inflating balloons at the two points.

In this case, it is possible to close the interior of the lumen by a simple method.

In the above configuration, preferably, a route ensuring step of ensuring, prior to the inserting step, a route in the lumen from the closed space to the opening, the route being separated from the luminal wall of the lumen, is further provided.

In this case, in the inserting step and the penetrating step, by operating the device inside the route ensured in the route ensuring step, it is possible to maintain the cleanliness of the device and the closed space.

In this case, the route ensuring step may be performed by inflating an elongated balloon extending from the closed space to the opening. In this case, it is possible to readily ensure a device insertion route.

In the first aspect above, the affected area may be the back side of the heart, and the lumen may be the esophagus.

In this case, even at a site on the back side of the heart, which has conventionally been difficult to approach from either the abdominal side or the back side of the patient, it is possible to readily approach the site with the surgical device from inside the esophagus and to treat the affected area from outside the heart.

A second aspect of the present invention is a medical device including a guide member that is inserted into a lumen; a first balloon provided at a distal end of the guide member and connected to a first flow path extending to a proximal end of the guide member; a second balloon provided on the guide member at a point separated from the first balloon on the proximal-end side and connected to a second flow path extending to the proximal end of the guide member; a third balloon extending along the guide member from a point between the first balloon and the second balloon to the proximal end and having a port for supplying or discharging fluid at the proximal end; and a cleansing flow path having a discharge port between the first balloon and the second balloon and extending to the proximal end of the guide member.

According to the second aspect of the present invention, the guide member is inserted into the lumen so that the first and second balloons are disposed in the vicinity of the affected area, and fluid is supplied to the first and second balloons via the first and second flow paths to inflate the balloons, whereby the interior of the lumen is closed at two points. Then, it is possible to cleanse the interior of the closed space by supplying cleansing liquid to and discharging the cleansing liquid from the closed space via the cleansing flow path. After cleansing, the third balloon is inflated, and the surgical device is inserted into the lumen through the interior of the third balloon to penetrate the third balloon and the luminal wall in the vicinity of the affected area. Thus, it is possible to advance the surgical device to the affected area and treat the affected area while maintaining the cleanliness of the surgical device and the affected area.

By approaching the affected area located outside the lumen from inside the lumen with the surgical device, it is possible to introduce the device and perform a procedure readily and with minimal invasiveness even at a site that is difficult to approach from the body surface.

In the second aspect above, the second balloon may be provided movably along a lengthwise direction of the guide member.

In this case, by inflating the third balloon while moving the second balloon from a position closer to the first balloon toward the proximal-end side, it is possible to inflate the third balloon uniformly from the distal end.

In the second aspect above, preferably, the third balloon is provided such that the third balloon is attachable to and detachable from the guide member.

In this case, after treating the affected area, by removing the third balloon from the lumen while keeping the guide member and the first balloon inside, it is possible to readily treat a puncture hole formed on the luminal wall.

In the second aspect above, a ring-shaped cover member that is attachable to and detachable from the outer circumferential surface of the second balloon and expandable in a radial direction in accordance with inflation of the second balloon may be further provided.

In this case, after treating the affected area, the second balloon is removed to the outside of the body, the cover member is placed on the second balloon and the second balloon is inserted into the lumen again, and the second balloon is inflated at the position where a puncture hole is formed on the luminal wall. Thus, it is possible to cover the puncture hole with the cover member expanded in the radial direction inside the lumen.

In this case, the cover member may be formed of a biodegradable material. This eliminates the need for a procedure for removing the cover member from the interior of the lumen after a medical operation.

According to the first and second aspects of the present invention, an advantage is afforded in that it is possible to approach a site and perform a procedure readily and with minimal invasiveness even if the site is difficult to approach from the body surface.

What is claimed is:

1. A medical device comprising:
   a guide member that is inserted into a lumen;
   a first balloon provided at a distal end of the guide member and connected to a first flow path extending to a proximal end of the guide member;
   a second balloon provided on a sheath that is placed over the guide member at a point separated from the first balloon on the proximal-end side and connected to a second flow path extending to the proximal end of the sheath;
   a third balloon extending along the guide member from a point between the first balloon and the second balloon to the proximal end and having a port for supplying or discharging fluid at the proximal end; and
   a cleansing flow path having a discharge port between the first balloon and the second balloon and extending to the proximal end of the guide member.

2. A medical device according to claim 1, wherein the second balloon is provided on the sheath that is movable along a lengthwise direction of the guide member.

3. A medical device according to claim 2, further comprising a ring-shaped cover member that is attachable to and detachable from the outer circumferential surface of the second balloon and expandable in a radial direction in accordance with inflation of the second balloon.

4. A medical device according to claim 3, wherein the cover member is formed of a biodegradable material.

5. A medical device according to claim 1, wherein the third balloon is provided such that the third balloon is attachable to and detachable from the guide member.

* * * * *